United States Patent
Stuck et al.

(10) Patent No.: US 8,923,662 B2
(45) Date of Patent: Dec. 30, 2014

(54) OPTICAL ENVIRONMENTAL SENSOR AND METHOD FOR THE MANUFACTURING OF THE SENSOR

(75) Inventors: Alexander Stuck, Wettingen (CH); Harald Walter, Horgen (CH); Marc Schnieper, Onex Genève (CH)

(73) Assignee: CSEM Centre Suisse d'Electronique et de Microtechnique SA—Recherche et Developpement, Hoffman Estates, IL (US)

( * ) Notice: Subject to any disclaimer, the term of this patent is extended or adjusted under 35 U.S.C. 154(b) by 43 days.

(21) Appl. No.: 12/384,771

(22) Filed: Apr. 8, 2009

(65) Prior Publication Data

US 2009/0263071 A1    Oct. 22, 2009

Related U.S. Application Data

(60) Provisional application No. 61/043,636, filed on Apr. 9, 2008.

(51) Int. Cl.
*G02B 6/00* (2006.01)
*G01N 21/77* (2006.01)

(52) U.S. Cl.
CPC .... G01N 21/7743 (2013.01); *G01N 2021/7723* (2013.01); *G01N 2021/7783* (2013.01)
USPC .............. 385/12; 385/37; 385/131

(58) Field of Classification Search
CPC ............ G01N 21/774; G01N 21/7743
USPC .................. 385/12, 37, 129–132
See application file for complete search history.

(56) References Cited

U.S. PATENT DOCUMENTS

| | | | |
|---|---|---|---|
| 3,998,591 A * | 12/1976 | Eckfeldt | 422/82.11 |
| 4,484,797 A | 11/1984 | Knop et al. | |
| 4,815,843 A | 3/1989 | Tiefenthaler et al. | |
| 5,006,716 A | 4/1991 | Hall | |
| 5,280,172 A * | 1/1994 | Di Bin et al. | 250/227.21 |

(Continued)

FOREIGN PATENT DOCUMENTS

| | | |
|---|---|---|
| EP | 1 862 827 A1 | 12/2007 |
| EP | 1 882 961 A1 | 1/2008 |

(Continued)

OTHER PUBLICATIONS

M.T. Gale, "Zero-Order Grating Microstructures" in R.L. van Renesse, Optical Document Security, 2nd Ed., pp. 267-287.

(Continued)

*Primary Examiner* — Uyen Chau N Le
*Assistant Examiner* — Chad H. Smith
(74) *Attorney, Agent, or Firm* — Soroker-Agmon

(57) ABSTRACT

A sensor which reacts on influences from an environment. The sensor includes a zero-order diffractive color filter. The zero-order diffractive color filter includes a high-index waveguide layer, a zero-order diffractive grating structure and a layer of an reactive material, wherein the reactive material is in contact with the environment and wherein the reactive material changes its optical properties upon interaction with the environment. The reactive material is embedded in the waveguide layer and/or the reactive material is located at a maximum distance d from the waveguide layer. The distancing is effected by an intra layer having a low index of refraction.

19 Claims, 18 Drawing Sheets

(56) References Cited

U.S. PATENT DOCUMENTS

| | | | |
|---|---|---|---|
| 5,774,603 A * | 6/1998 | Moore et al. ................... | 385/12 |
| 5,925,878 A | 7/1999 | Challener | |
| 7,142,296 B2 * | 11/2006 | Cunningham et al. ......... | 356/326 |
| 7,854,505 B2 * | 12/2010 | Cunningham et al. .......... | 351/44 |
| 2003/0017580 A1 | 1/2003 | Cunningham et al. | |
| 2004/0132214 A1 | 7/2004 | Lin et al. | |
| 2004/0247229 A1 | 12/2004 | Tiefenthaler | |
| 2006/0062509 A1 | 3/2006 | Krol et al. | |
| 2007/0047874 A1 | 3/2007 | Schulz | |

FOREIGN PATENT DOCUMENTS

| | | |
|---|---|---|
| EP | 1 990 661 A1 | 11/2008 |
| WO | WO 03/064995 A2 | 8/2003 |
| WO | WO 2006/038120 A1 | 4/2006 |
| WO | 2007/0137438 | 12/2007 |
| WO | WO 2008/069572 A1 | 6/2008 |
| WO | WO 2008/123927 A1 | 10/2008 |

OTHER PUBLICATIONS

"Optical Sensors and Biosensors Based on Sol-Gel Films'", Paula C.A. Jerónimo et al., Talanta, 2007, vol. 72, pp. 13-27.

Block et al . "A Sensitivity Model for Predicting Photonic Crystal Biosensor Performance" IEEE Sensors Journal, vol. 8, No. 3, Mar. 2008.

Zhang et al."High sensitivity photonic crystal biosensor incorporating nanorod structures for enhanced surface area" Sensors and Actuators B 131 (2008) 279-284.

European Search Report dated Jan. 16, 2013 for European Application No. 09157610.8, filing Aug. 4, 2009.

Knop. K; Diffraction gratings for color filtering in the zero diffraction order; Applied Optics, vol. 17, No. 22; Nov. 15, 1978.

Lukosz. W et al; Sensitivity of integrated optical grating and prism couplers as (bio)chemical sensors; Sensors and Actuators; Elsevier Switzerland; vol. 15, No. 3; Nov. 1, 1988; pp. 273-284.

* cited by examiner

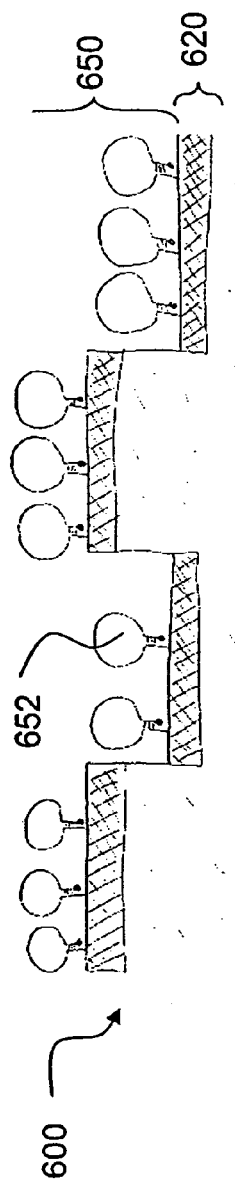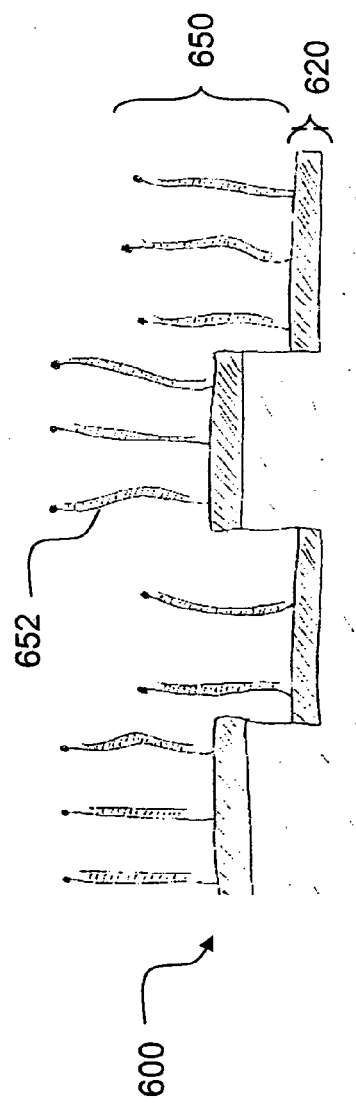

OPTICAL ENVIRONMENTAL SENSOR AND METHOD FOR THE MANUFACTURING OF THE SENSOR

CROSS-REFERENCE TO RELATED APPLICATIONS

This patent application claims priority from U.S. Provisional Patent Application No. 61/043,636, filed on Apr. 9, 2008, the U.S. Provisional Patent Application which is incorporated in its entirety herein by reference.

BACKGROUND OF THE INVENTION

1. Field of the Invention

This invention relates to the field of environmental sensors and particularly, optical environmental sensors.

2. Discussion of Related Art

Zero-order diffractive color filter (ZOF), also known as Zero Order Device (ZOD) or resonant grating or guided mode resonant filter, are made by diffractive gratings, such as parallel or crossed gratings, having a depth t and a period Λ usually smaller than a wavelength of light for which the filter is designed or isotropic microstructures with a short range ordering but long range disordering surrounded with material of lower refractive indices than the diffractive gratings.

As schematically shown in more detail in FIG. 1A, a ZOF 100 includes at least one grated structure 110 surrounded by a material 120, such as air, having a low-index of refraction ($n_{low}$) compared to grated structure 110 having a high-index of refraction ($n_{high}$), wherein e.g., $n_{high} > n_{low} + 0.2$. In order for strong zero-order diffraction to take place, additional parameters have to be adjusted including: the grating period (Λ); the grating depth (t); the waveguide layer thickness (c); the fill factor or duty cycle and the grating profile or shape. As configured, grated structure 110 may act as a grated waveguide layer 130. ZOF 100 illuminated by polarized or unpolarized polychromatic light 50 (FIG. 1B) transmit and/or reflect principally the zero order of the light incident on ZOF 100. Accordingly, grated waveguide layer 130 acts like a color filter by reflection and/or transmission, because the zero order diffraction of incident light is clearly separated from higher diffraction orders. More specifically, a part of light incident onto ZOF 100 is diffracted, whereby diffraction orders higher than 0 are coupled by evanescent diffracting order into grated high-index waveguide layer 130 and then rediffracted out, whereas the remainder of the incidence light, i.e., diffraction order of 0, is transmitted through and/or reflected from ZOF 100 into light 52 and light 51, respectively. The coupling of light into grated waveguide layer 130 occurs at certain wavelengths and at a certain angular orientation φ where resonance causes destructive interference. Thus, ZOF 100 possess characteristic reflection and/or transmission spectra depending on a viewing angle Θ and the orientation φ of the grating lines with respect to the observer, not shown.

For each pair of angles they directly reflect a particular spectral range or color. As long as the materials used possess no absorption the transmission spectra are the complement of those in reflection. For example, as schematically shown in FIG. 1C and FIG. 1D, the reflected and/or transmitted light 51 and 52 may be of the blue and yellow wavelength, respectively. In contrary to higher order diffraction devices, for a ZOF such as ZOF 100, light is reflected at a viewing angle which is equal to the incidence angle. Documents related to color filters based on ZOF are discussed in the following paragraphs.

In U.S. Pat. No. 4,484,797 to Knop et al. a variable index-of-refraction optical medium of certain minimum thickness and periodicity with respect to the wavelength of incident light is disclosed, if it meets certain specified constraints with respect to (1) relative indices-of-refraction of both its internal structure and that of its surroundings and (2) relative values of incident wavelength to periodicity and the relative indices-of-refraction-operates to produce both angularly-dependent subtractive-color filter reflection spectra and subtractive-color filter transmission spectra in accordance with its physical parameters.

FIG. 2A, FIG. 2B and FIG. 2C schematically illustrate various possible profiles for grated structures 110, namely rectangular, generally sinusoidal and triangle shaped profiles, respectively.

WO2006/038120 to Walter discloses a security device including a first zero order diffractive microstructure on a substrate, a second zero order diffractive microstructure, and an intermediate light transmissive layer separating the two diffractive microstructures. The disclosed security device allows interference of visible light to take place.

EP1882961 to Walter et al. discloses a Zero-order diffractive filter including a first layer with a periodic diffractive microstructure, forming a waveguide, and at least one adjacent second layer, wherein the first layer has a refractive index that is higher than the refractive index of the second layer by at least 0.2. At least one of the second layers is a porous layer including nanopores. The period of the diffractive microstructure is between 100 nm and 3000 nm.

EP1862827 to Stuck et al. discloses a zero order diffractive filter for polarized or unpolarized polychromatic light, including a grating line microstructure formed by a surrounding medium with a low index of refraction n low and a waveguide layer with a high index of refraction n high, the grating lines having a grating period Λ that is smaller than the wavelength of light for which the filter is designed. A plurality of single nanostructures with dimensions in the nanometer range is superposed on a first interface between the surrounding medium and the waveguide layer. In one embodiment, the zero-order diffractive filter includes an interface between a low refraction index medium and the waveguiding layer that is nanostructured.

WO03/064995 to Cunningham et al. describes a label-free guided mode resonant filter biosensor using a linear one-dimensional grating surface structure. The shift of a narrow reflection peak is measured. The peak shift is caused by a change in the index of refraction at the surface of the grating due to the interaction of biological substances with the sensor. Due to the narrowness of the reflection peak and the minor peak shift, the filter shows no visible color effect. Further these filters work in the near infra red spectral range.

EP 1990661 to Blondiaux et al. discloses an isotropic zero-order diffractive color filter, a method to manufacture an embossing tool and a method to manufacture such a filter. The zero-order diffractive color filter includes diffractive microstructures and a wave-guiding layer, wherein the diffractive microstructures possess a short range ordering over at least four times the period of the microstructures, and the diffractive microstructures possess a long range disordering over length scales of more than 100 micron.

Further details concerning zero-order diffractive filters can be found in M. T. Gale, "Zero-Order Grating Microstructures" in R. L. van Renesse, Optical Document Security, 2nd Ed., pp. 267 287. The correct choice of grating period, depth and profile with a defined number of high and low material indices transitions can make a specified color band pass filter or notch filter.

SUMMARY OF THE INVENTION

Positional terms such as "upper", "lower", "right", "left", "bottom", "below", "lowered", "low", "top", "above", "elevated", "high", "vertical" and "horizontal" as well as grammatical variations thereof as may be used herein do not necessarily indicate that, for example, a "bottom" component is below a "top" component, or that a component that is "below" is indeed "below" another component or that a component that is "above" is indeed "above" another component as such directions, components or both may be flipped, rotated, moved in space, placed in a diagonal orientation or position, placed horizontally or vertically, or similarly modified. Accordingly, it will be appreciated that the terms "bottom", "below", "top" and "above" may be used herein for exemplary purposes only, to illustrate the relative positioning or placement of certain components, to indicate a first and a second component, or to do both.

It should be understood that an embodiment is an example or implementation of this invention or the inventions. The various appearances of "one embodiment," "an embodiment" or "some embodiments" do not necessarily all refer to the same embodiments.

Although various features of this invention may be described in the context of a single embodiment, the features may also be provided separately or in any suitable combination. Conversely, although this invention may be described herein in the context of separate embodiments for clarity, this invention may also be implemented in a single embodiment.

It should be noted the terms "low-index" and "high-index" with reference to refraction as used herein should be referred to in relation to or relative to each other. For example, a low-index material has a lower index of refraction than a feature being disclosed for example, as a high-index waveguide layer.

The term "reactive material" as used herein, refers to any material which may change its optical properties in general and in particular its index of refraction due to changes in a reactive material environment with which the reactive material may engage such as, for example, temperature, pressure, relative humidity, chemical composition, electricity, biological elements, immersion in various fluids, exposure to electromagnetic radiation (e.g., visible light, UV, X-ray, infrared light), and the like. The sensor may, for example, change its optical properties due to changes in pH values of, e.g., an aqueous solution, in which the sensor may be immersed. Therefore, a change in the color of reflected and/or transmitted light may provide an indication of the corresponding change in the pH value of the same solution.

SUMMARY OF THIS INVENTION

With a change of the optical properties and/or thickness of a reactive material in a layer above or a top layer or a layer below or a bottom layer, a high-index waveguide layer of a zero-order diffractive color filter (ZOF) can change the color of light reflected from and/or transmitted through the ZOF. Correspondingly, a ZOF according to embodiments of this invention comprising the reactive material may act as an optical environmental sensor or sensor.

In embodiments of this invention, the sensor thus comprises a (ZOF) which comprises a high index of refraction waveguide layer, a zero-order diffractive grating structure and a layer of a reactive material. In embodiments of this invention, the ZOF comprises reactive material, which when interacting with the environment, changes its optical properties.

In embodiments of this invention, the reactive material is embedded in or located on at least one of the following locations of the ZOF: the waveguide layer, and at a maximum distance d from the waveguide layer.

In embodiments of this invention, the reactive material constitutes or forms the high-index waveguiding layer, i.e., the high-index waveguiding layer may include the reactive material.

In embodiments of this invention, the distance d may be effected by an intra layer which may have a low index of refraction.

In embodiments of this invention, the high index of refraction waveguide layer and the zero-order diffractive grating structure may be a single layer.

In embodiments of this invention, the high index of refraction waveguide layer and the zero-order diffractive grating structure are at least two distinct layers.

In embodiments of this invention, the ZOF may be mounted on a low refractive index material base layer or a substrate that can be bulky in form.

In embodiments of this invention, the maximum distance d is, for example, 2000 nm.

In embodiments of this invention, the period of the zero-order diffractive grating structure may be in the range of, e.g., 300 nm to 500 nm.

In embodiments of this invention, the reactive layer when in contact with the environment may be capable of interaction with gaseous and/or liquid and/or solid components of the environment and/or with electromagnetic radiation propagating in or pervading the environment.

In embodiments of this invention, the reactive layer in contact with the environment may have a porous structure in order to enhance the reactive surface.

In embodiments of this invention, the reactive layer comprises swelling material.

In embodiments of this invention, the sensor may be of the form of pigments having a lateral size of $2 \times 2$ $\mu m^2$ up to $200 \times 200$ $\mu m^2$.

In embodiments of this invention, the reactive layer in contact with the environment may include interaction-promoting molecules in order to enable a selective binding of corresponding molecules.

This invention further discloses the use of the sensor according to embodiments of this invention. For example, the use may include observing and/or sensing the spectrum change of reflected and/or transmitted radiation spectrum.

In embodiments of this invention, the use may include observing and/or sensing the color change of reflected and/or transmitted light.

In embodiments of this invention, the use may include sensing and/or utilizing the reflected light from the backside of the sensor.

In embodiments of this invention, the use may take place in association with printing inks.

BRIEF DESCRIPTION OF THE DRAWINGS

These and further features and advantages of this invention will become more clearly understood in view of the following description of some embodiments by way of example only, with reference to the accompanying figures (FIGs), wherein:

FIG. 6A is a schematic side-view illustration of an optical environmental sensor, prior to being subjected to environmental changes, according to a yet other embodiment of this invention;

FIG. 6B is a schematic side-view illustration of the optical environmental sensor, after being subjected to environmental changes, according to the embodiment of FIG. 6A;

DETAILED DESCRIPTION OF THE INVENTION

Figure 1B:
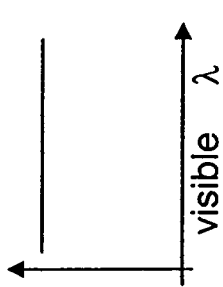
FIG. 1B is a schematic illustration of the spectrum of white light incident on the ZOF.
Figure 1C:
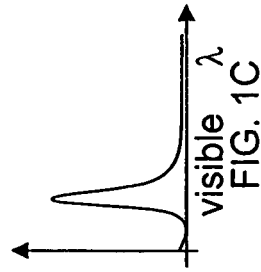
FIG. 1C is a schematic illustration of the spectrum of light reflected from the ZOF.
Figure 1D:
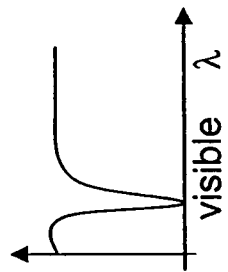
FIG. 1D is a schematic illustration of the spectrum of light transmitted through the ZOF.
Figure 1A:
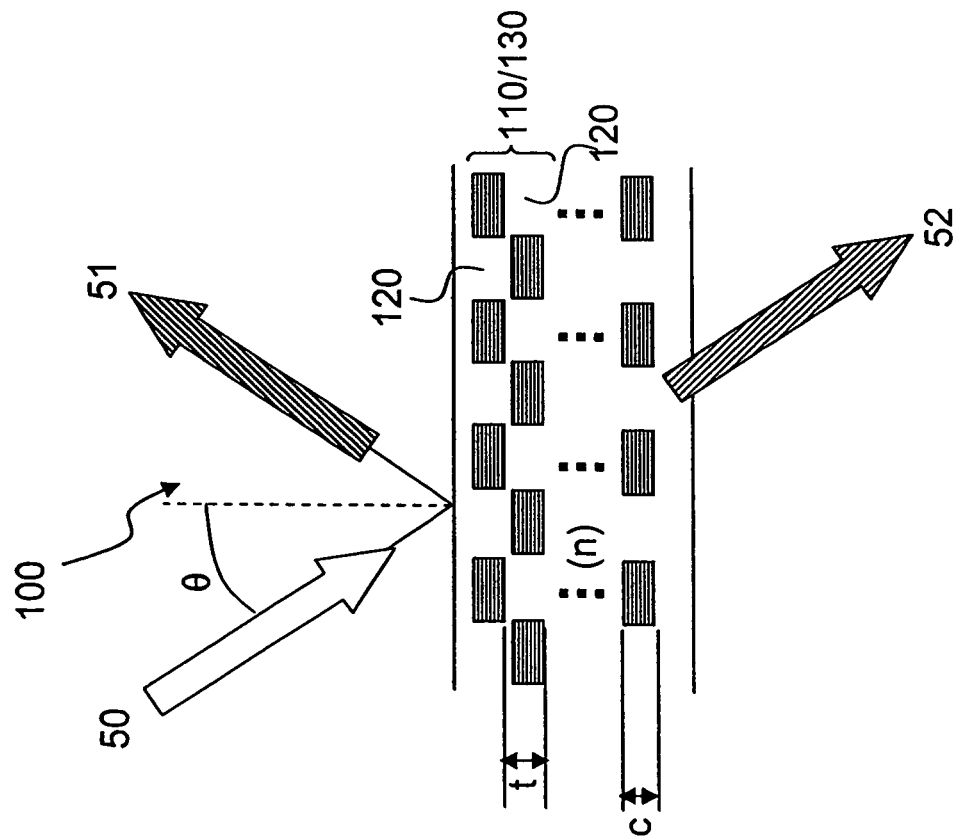
FIG. 1A is a schematic side-view illustration of a Zero-Order Diffractive Filter (ZOF) as known in the art.
Figure 2C:
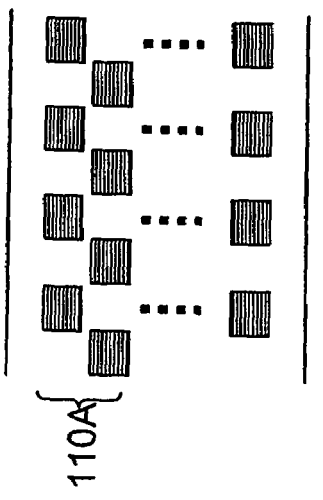
FIG. 2C is a schematic side-view illustration of a third structure of a high-index waveguide layer as known in the art.
Figure 2B:
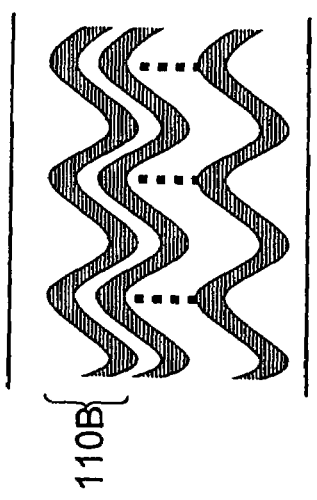
FIG. 2B is a schematic side-view illustration of a second structure of a high-index waveguide layer as known in the art.
Figure 2A:
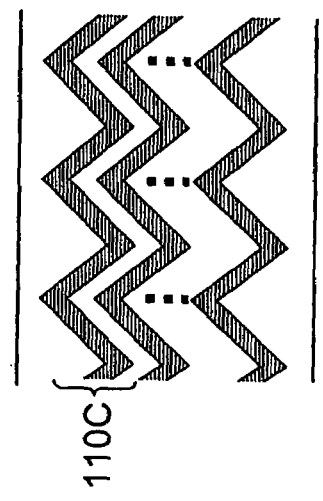
FIG. 2A is a schematic side-view illustration of a first structure of a high-index waveguide layer as known in the art.
Figure 3:
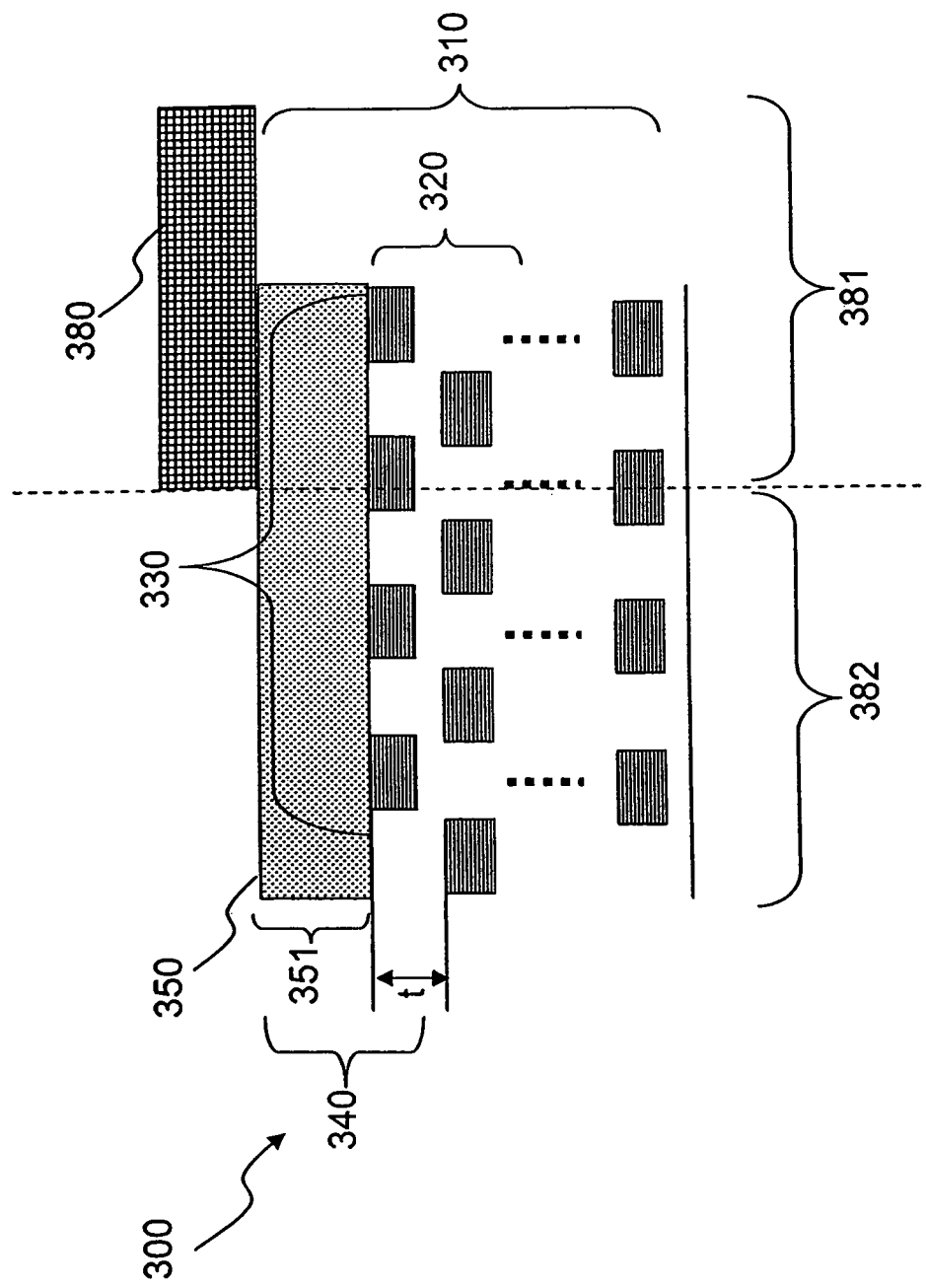
FIG. 3 is a schematic side-view illustration of an optical environmental sensor, according to an embodiment of this invention.

Referring to FIG. 3, an optical environmental sensor or sensor according to an embodiment of this invention such as, for example, sensor 300 comprises a zero-order diffractive colour filter (ZOF) 310 that includes a high-index waveguide layer 320 comprising a zero-order diffractive grating structure 330 surrounded by at least one low-index material 340. Sensor 300 further comprises a reactive material 350 which, when interacting with the environment, may change its optical properties and thus the filter properties of ZOF 310 accordingly.

Figure 4:
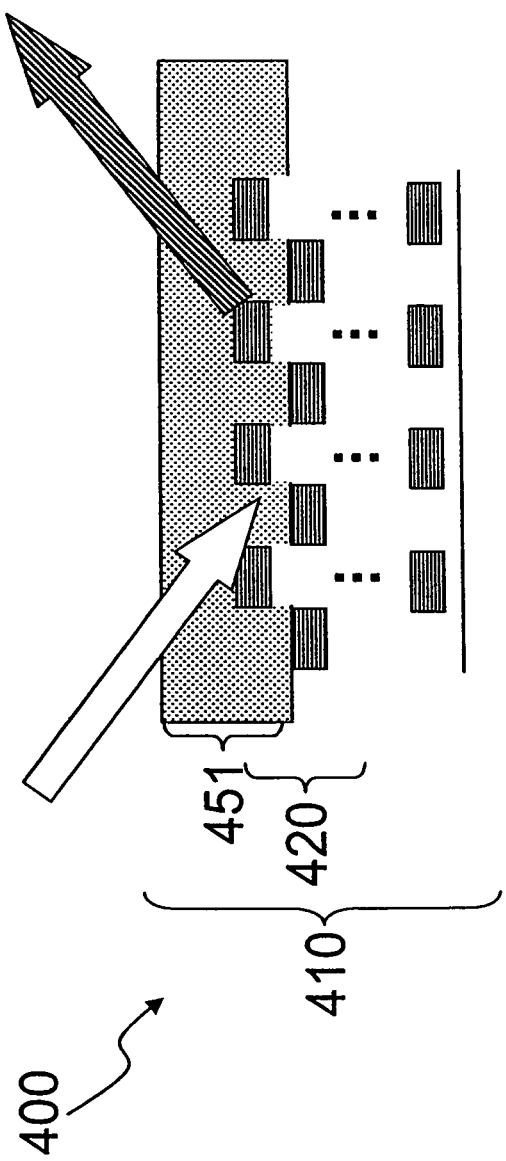
FIG. 4 is a schematic side-view illustration of an optical environmental sensor, according to another embodiment of this invention.

According to embodiments of this invention, reactive material 350 may have the form of a layer such as, for example, a layer 351, which may form or constitute, e.g., a cover for sensor 300. According to embodiments of this invention, reactive material 350 may be a part of or embedded in low-index material 340. Alternatively, for example as schematically illustrated in FIG. 4, a sensor 400 may comprise a reactive material 550 constituting or being embedded in low-index material 451.

According to embodiments of this invention, a low-index material such as, for example, low-index material 340, may be in the form of a bulky substrate comprising, for example, glass plate or polymer foil. Alternatively, low-index material 340 may be layered.

According to embodiments of this invention, the period of the diffractive gratings of a high-index waveguide layer such as, for example, high-index waveguide layer 320 and/or high-index waveguide layer 420 may be, for example, between 300 nm and 2200 nm, or for example, preferably between 300 nm and 1700 nm or for example, particularly preferred between 300 nm and 500 nm. According to embodiments of this invention, the structure depth t of the diffractive gratings may be, for example, between a few nanometers to some micrometers or for example, preferably between 50 nm and 300 nm. The number of high-index waveguide layers may have no fixed upper limit, i.e., sensor 300 for example, may comprise at least one high-index waveguide layer 320. According to embodiments of this invention, the difference in refractive index between for example high-index waveguide layer 320 and low-index material 340 may be, e.g., at least 0.2.

Figure 5:
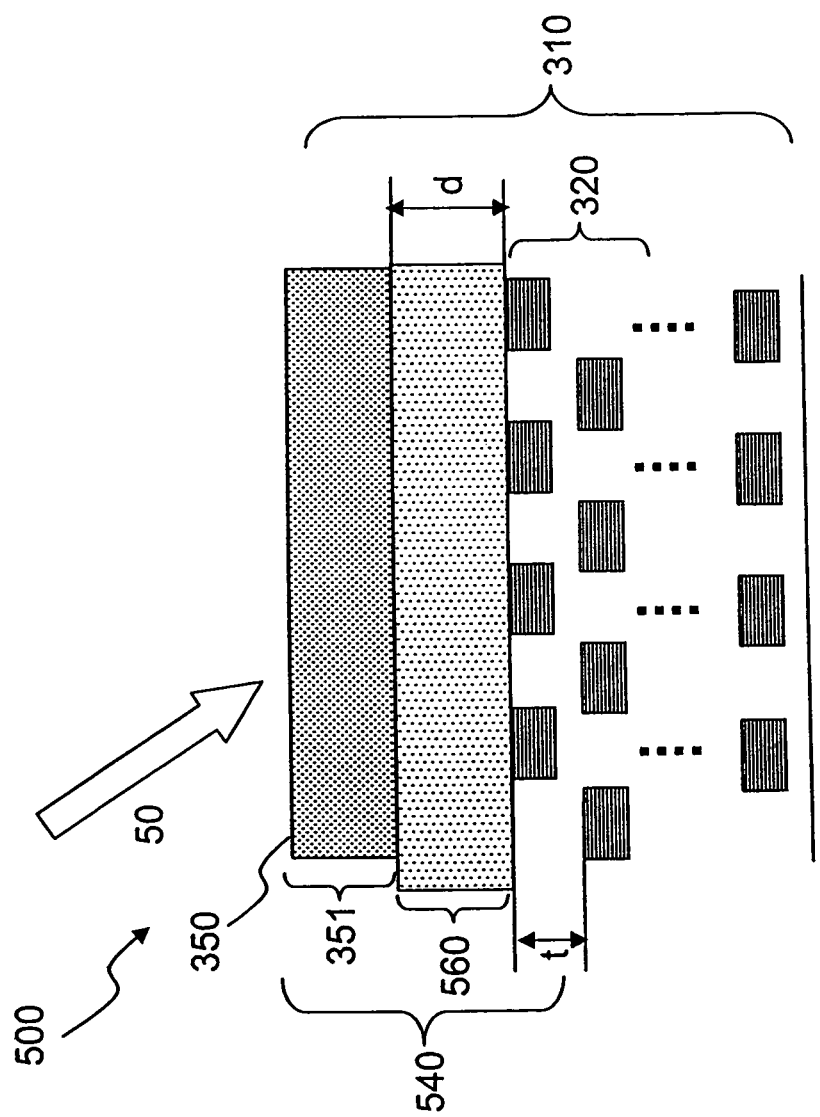
FIG. 5 is a schematic side-view illustration of an optical environmental sensor, according to an alternative embodiment of this invention.

Referring to FIG. 5, in embodiments of this invention, a reactive material such as reactive material 350 for example may be at various distances away from the interface between high-index waveguide layer 320 and low-index layer 340. For example, reactive material 350 may be at a maximum distance away from the interface between high-index waveguide layer 320 and low-index material 340, wherein the maximum distance d may for example be 2000 nm, 300 nm, 100 nm, 30 nm, or 15 nm. Different distances d may result in a corresponding modification of the optical properties of sensor 300. For example, absorption properties of ZOF 300 for light incident on the latter may be modified, which may result in a modification of the light-transmitting and/or reflecting properties of ZOF 300. Examples of changes of optical properties include, inter alia, increase or decrease of the absorption strength and/or a shift of the absorption spectrum.

According to embodiments of this invention, a sensor such as sensor 500 may additionally include at least one spacer layer 560 between high-index waveguide layer 320 and active material 350 which may be used to enhance changes in color effects in response to environmental changes. Spacer layer 560 may, for example, be made of thin films and have a relatively low or high refractive indices. Spacer layer 560 may, for example, comprise at least one of the following materials $MgF_2$, or $SiO_2$ or $Al_2O_3$, many polymers or some porous material and/or ZnS, $TiO_2$ or $ZrO_2$ or any suitable combination thereof.

A reactive material according to embodiments of this invention, such as reactive material 350, may be made of porous material to increase the potential changes in optical properties of reactive material 350 in response to environmental changes. Non-limiting examples of such porous material include Sol-Gel and/or porous Silicon layer and/or any porous aerogel.

Additionally or alternatively, Sol-gel materials doped with chemical sensitive species may also be used to implement a reactive material such as, for example, reactive material 350. Examples of such materials are outlined in "Optical sensors and biosensors based on sol-gel films", Paula C. A. Jeronimo, Talanta, 2007, vol. 72, pp. 13-27. A reactive material according to embodiments of this invention may for example be implemented by using pH-sensitive dyes embedded in a sol-gel matrix since the reactive material exhibits a shift in the absorption spectrum in response to a change in pH and/or exposure to gas.

Additionally or alternatively, a reactive material may comprise porous birefringent materials. Organic or water vapors may condensate into the pores and change both the refractive index and the anisotropy of the material. Due to the now birefringent properties of a sensor according to an embodiment of this invention, such as ZOF 300, the reflected spectrum may depend on the amount of vapors trapped into the porous material of reactive material 350.

Additionally or alternatively, a reactive material, for example reactive material 350, may include swelling material. The optical properties of such swelling materials may change due to a change in the thickness of the material. Also, a change in thickness of a reactive material according to an embodiment of this invention may cause a different resonant condition inside, e.g., sensor 300. For example, in some embodiments of this invention, reactive material 350 of ZOF 300 may surround high-index grating layer 320 and/or may be the material of which high-index grating layer 320 may be made. The thickness and/or the grating period would depend on the expansion of the swelling material. Thus configured, the optical properties of ZOF 300 may alter due to change, for example, in humidity and/or the chemical species of the environment being engaged with ZOF 300.

Swelling materials could be use as the reactive material in the sensitive layer or in the core waveguide or as an interlayer between two waveguide layers in a multi layer setup as shown in FIG. 1. Preferably, the thickness of the interlayer is in the range of 30 nm to 2000 nm, particularly between 50 nm and 500 nm and particularly preferred between 80 nm and 200 nm.

Referring to FIG. 6A and to FIG. 6B, according to embodiments of this invention, a sensor 600 may comprise a reactive material 650 having a top layer employing interaction-promoting molecules 652. Interaction-promoting molecules 652 are adapted to enable selective binding with molecules. Non-limiting examples of such interaction-promoting molecules 652 include single stranded DNA and/or antibodies, and/or Biotin and/or Streptavidin, and the like, all of which may be linked with the top surface of reactive material 650 and/or of the high-index waveguide layer 620 of sensor 600. The linking may be accomplished covalently with one end of interaction-promoting molecule 652. As schematically illustrated, the top layer may have a grated structure or be at least approximately relatively flat. In certain embodiments, the top layer is porous, thus for example enabling the coupling of the DNA to the surface of the pores. On the free end of the single stranded DNA, a dye or chromophor may be linked.

FIG. 6A schematically illustrates interaction-promoting molecules 652 embodied by complementary DNA single strands prior to being in contact with a solution (not shown). FIG. 6B schematically illustrates the DNA single strands after hybridization due to contact with the solution (not shown). Single stranded DNA is a flexible polymer. In embodiments of this invention, the sequence of the DNA may be chosen so that the strand forms a hairpin-like loop and the dye or chromophor of the strand may be in closer proximity to high-index waveguide layer 620 (FIG. 6A) in comparison to the position in which the dye or the chromophor would be if the DNA would not form a hairpin-like loop (FIG. 6B). The dye or chromophor damps the light in the waveguide with a wavelength which lies in the absorption band of the dye or chromophor. By immersing sensor 600 into a solution containing a DNA single strand which is complementary to the DNA strand linked to the top layer of reactive material 650, both the strand linked to the top layer and the strand in the solution hybridize and form a double strand, as schematically illustrated in FIG. 6B, i.e., the hairpin-like loop may thus open and the dye or chromophor is kept at a larger distance away from high-index waveguide layer 620 because double stranded DNA is a stiff polymer. Thus, by immersing sensor 600 into the solution, the interaction between the dye or chromophor and the light confined in high-index waveguide layer 620 is reduced. Accordingly, immersing sensor 600 into the solution leads to a color change. Only if the complementary DNA strand is in the solution the sensor may exhibit an observable color effect. This principle is somewhat similar to molecular beacons which switch a fluorescence signal. These molecules can be switched on or off by hybridizing with complementary DNA strands.

It should be noted that the area of a ZOF according to an embodiment of this invention may not be restricted and may range from a few periods (e.g., ~3 microns) to several cm, whereby the intended application may define the area size. For example, a ZOF according to an embodiment of this invention may embody a pigment incorporating environmental sensing function. Sensor 300 may be, for example, of a rectangular shape, a generally circular shape, or any other geometric shape. For example, sensor 300 may have a lateral size ranging, e.g., between $2\times2$ $\mu m^2$ and $200\times200$ $\mu m^2$, or preferably between $4\times4$ $\mu m^2$ and $40\times40$ $\mu m$. The thickness of a sensor according to an embodiment of this invention embodying a pigment may be sufficiently thin to render flakes. The thickness may, for example, range between 50 nm and 2000 nm, or preferably between 100 nm and 800 nm and especially between 150 nm and 500 nm. Sensors according to embodiment of this invention may thus be printable by embedding such pigments in an appropriate formulation. After printing and drying of the sensors, the matrix in which the pigments are embedded should be permeable enough to enable interaction with the environment for optical sensing. The production of ZOF-pigments is for example described in WO2007/137438.

For the human eye, it is easier to see differences in color than to quantify the observed colors. Thus, in an embodiment of this invention, a part 381 of a sensor such as, for example, sensor 300 may be encapsulated by a protective cover 380 to realize a reference color effect with respect to a complementary non-encapsulated part 382 of sensor 300. Accordingly, encapsulated part 381 is a non-sensing part whereas non-encapsulated part 382 remains the sensing part of sensor 300. The optical properties of encapsulated part 381 are not modified upon engaging sensor 300, for example with the gas and/or liquid and/or radiation to be detected, whereas the optical properties of non-encapsulated part 382 are modified. Thus, respective differences in color may become observable or detectable. Encapsulation may be achieved with a protective cover such as, for example, a glass plate substrate and/or polymer foil substrate covering a part of sensor 300 to protect the underlying layers, for example from UV radiation. Protective cover 382 may be engaged with sensor 300 for encapsulation, for example with a ring-shaped glue or adhesive to fix protective cover 380 to sensor 300. It should be noted that in some embodiments, dyes and/or chromophores may be embedded or at least partially make up high-index waveguide layer 620. Additionally or alternatively, high-index waveguide layer 620 may be of dyes and/or chromophores (not shown).

Figure 7A:
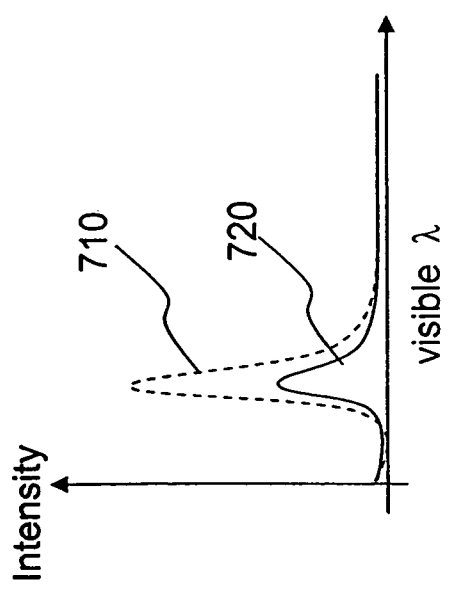
FIG. 7A is a schematic illustration of the differences of spectra of light transmitted through an optical environmental sensor according to an embodiment of this invention, before and after subjected to environmental changes, according to an embodiment of this invention.
Figure 7B:
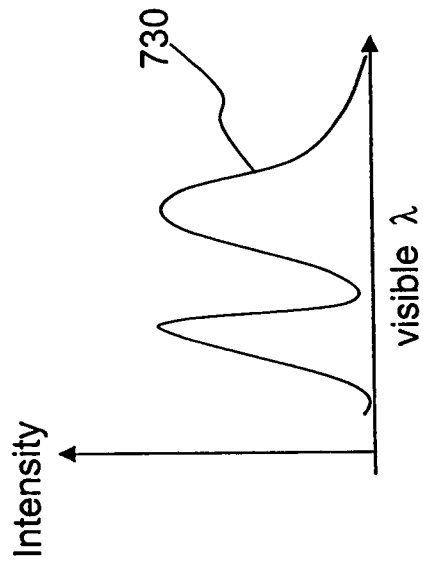
FIG. 7B is a schematic illustration of the differences of spectra of light reflected from an optical environmental sensor according to an embodiment of this invention, after subjected to environmental changes, according to an embodiment of this invention.

Referring to FIG. 7A, as schematically illustrated, by changing the environment (e.g., changing the surrounding liquid and/or providing gazes) with which a ZOF according to an embodiment of this invention such as, for example, ZOF 350, may be engaged, the transmitted spectra of light may correspondingly modify from a first transmission spectra 710 to a second transmission spectra 720, wherein the second transmission spectra 720 may exhibit an attenuation in intensity compared to the first transmission spectra 710. Referring now to FIG. 7B, the spectrum 730 of light reflected from a ZOF according to an embodiment of this invention, for example ZOF 350, may have distinguishable colors (adjunction of an emission).

Figure 8:
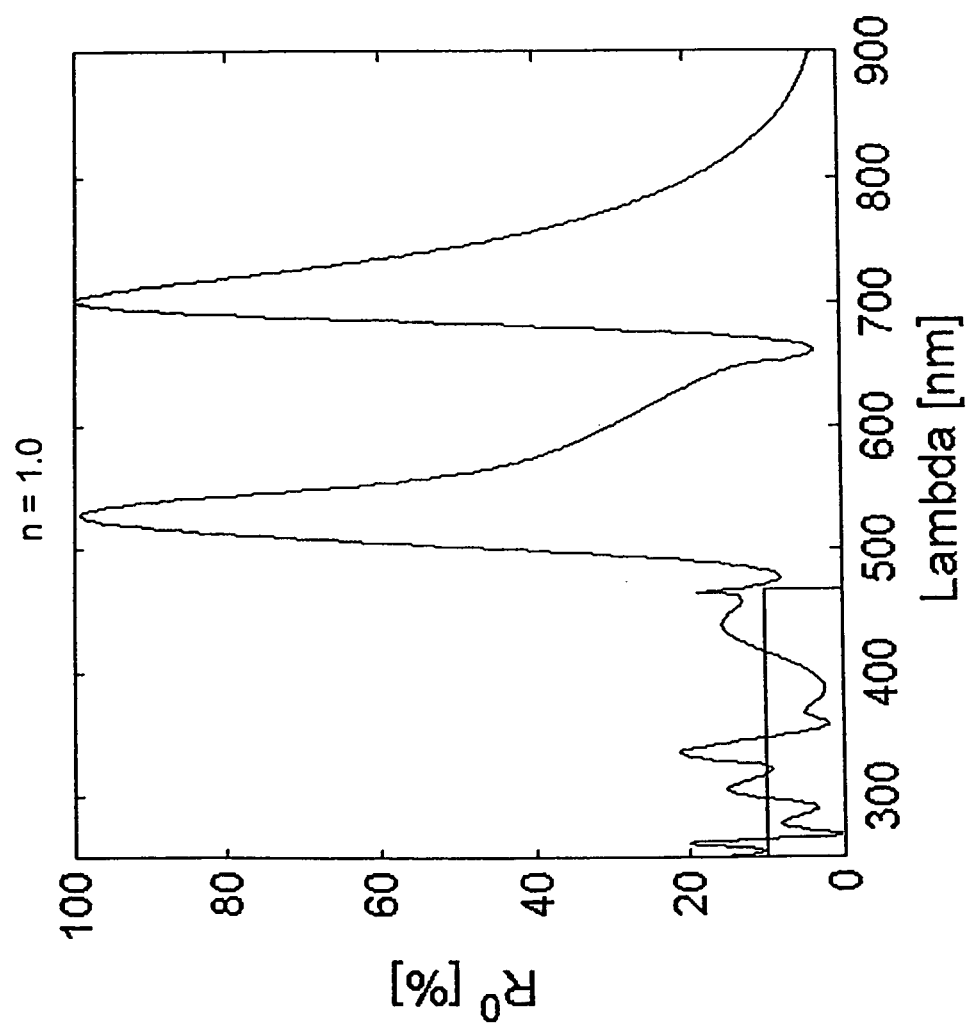
FIG. 8 to FIG. 10 each is a schematic illustration of a spectra of light reflected from an optical environmental sensor subjected to media having respective indices of refraction, according to an embodiment of this invention.
Figure 9:
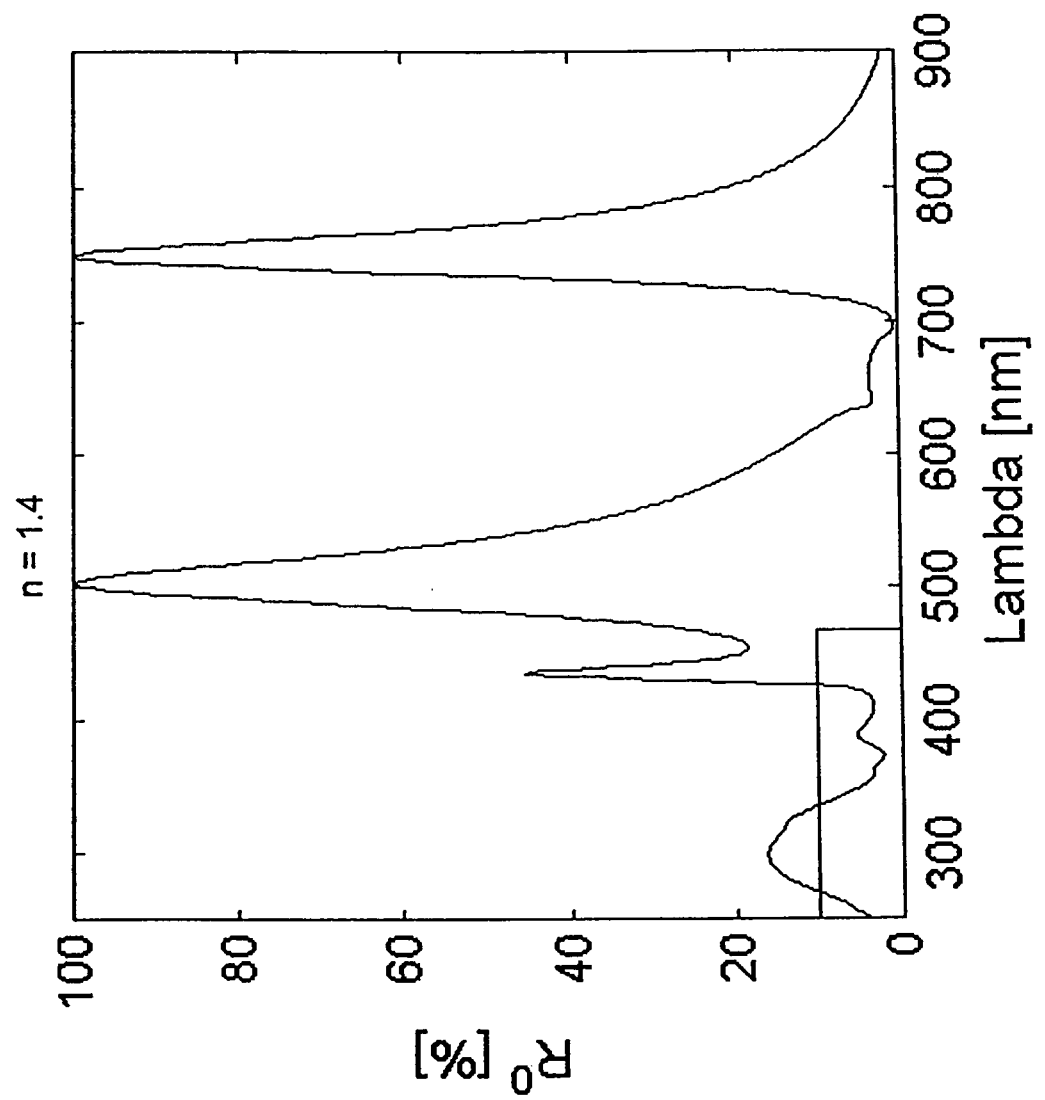
Figure 10:
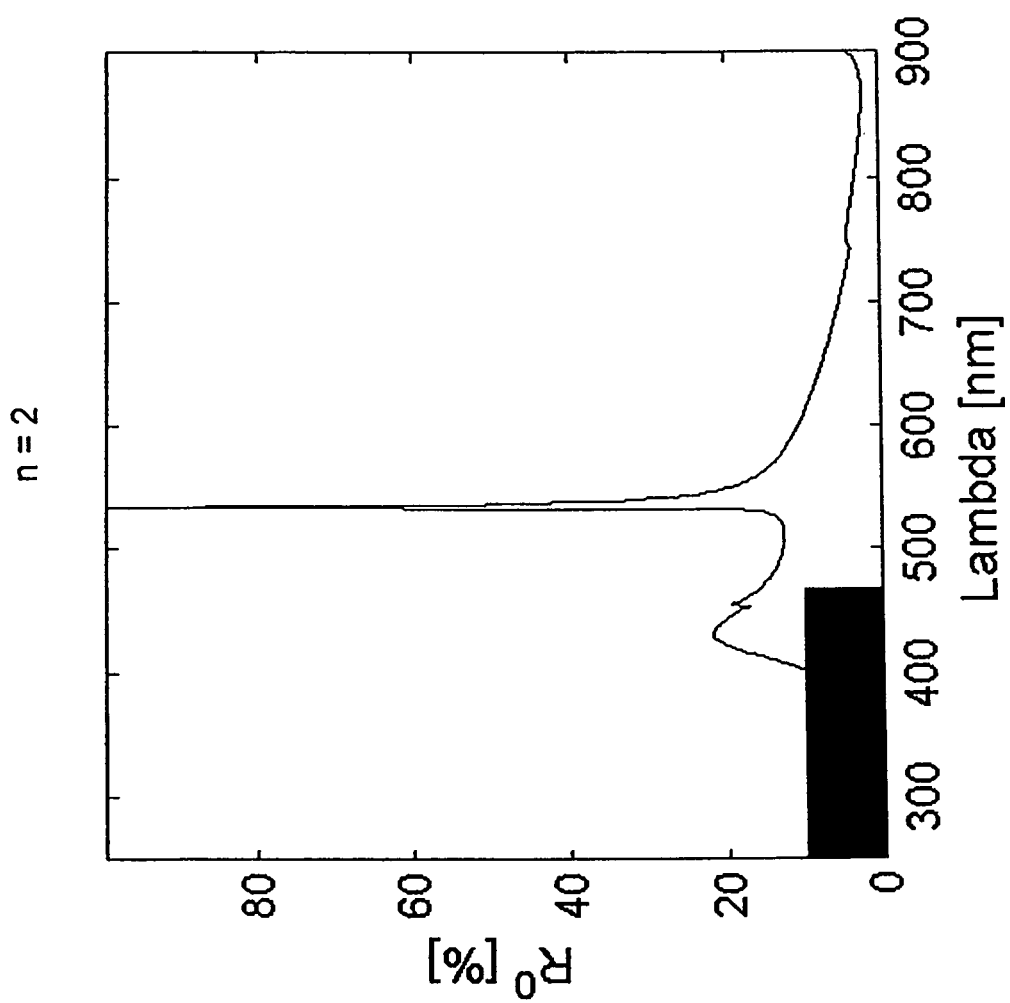
Figure 11:
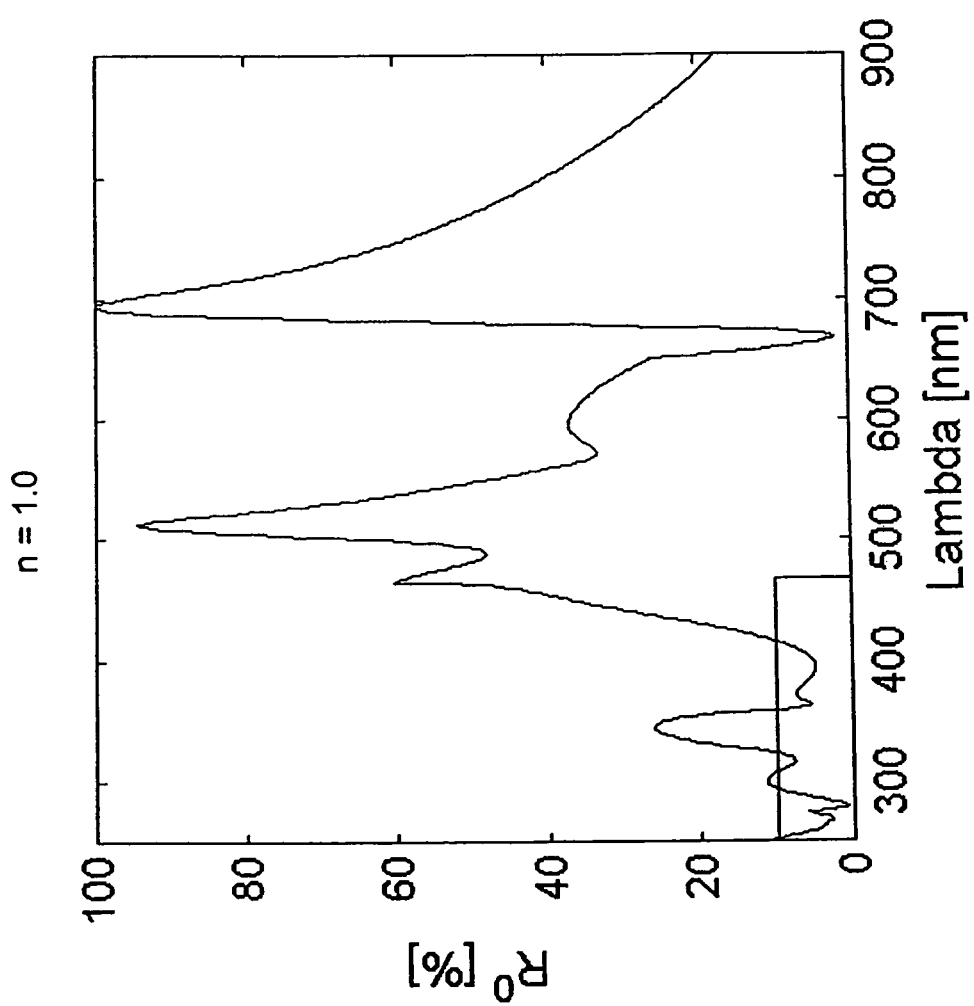
FIG. 11 to FIG. 13 each is a schematic illustration of a spectra of light reflected from another optical environmental sensor subjected to media having respective indices of refraction; according to an embodiment of this invention.
Figure 12:
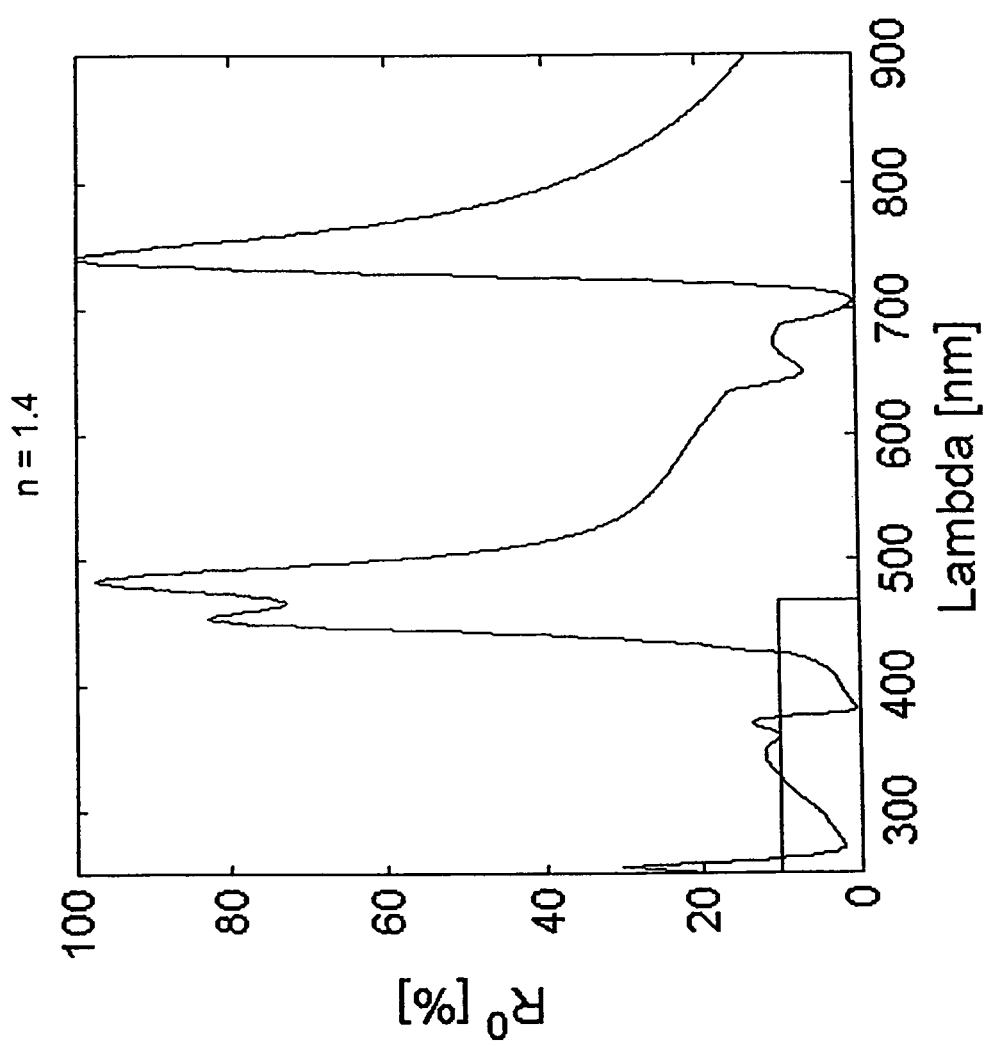
Figure 13:
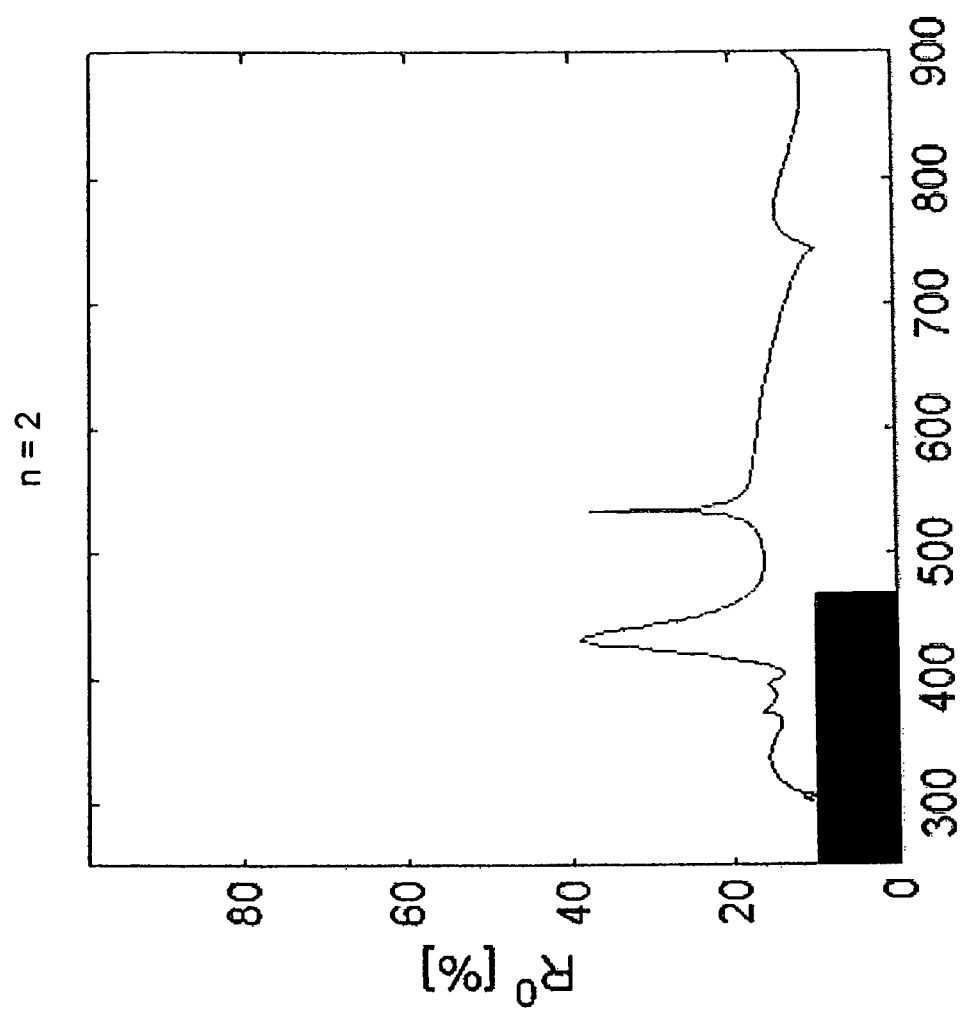

Referring to FIG. 8, FIG. 9 and FIG. 10, each of which schematically illustrates an example for changes of calculated reflection spectra for a sensor according to an embodiment of this invention, (e.g., sensor 300) wherein the reactive material 350 for example is subjected to different environmental media. The refractive index of the media are 1.0 (air), 1.4 and 2.0, wherein the parameters of high-index waveguide layer 320 are as follows: Period=450 nm, grating depth=120 nm and 175 nm, grating shape rectangular, incidence angle of light=15°, index of refraction of high-index waveguide layer 320 $n_{high}$=2.3 and thickness of high-index waveguide layer 320 c=100 nm. The changes in calculated reflected light spectra for the respective indices of refraction can readily be seen in FIG. 8, FIG. 9 and FIG. 10. However, the shown examples are not to be construed to be limiting of the possible changes in color that may be achieved with a sensor according to embodiment of this invention as different structures of ZOF (period, depth, number of staked ZOFs, thickness of the high refractive structures) will give different color change suited to the application and environment. For example, as schematically illustrated in FIG. 11, FIG. 12 and FIG. 13, other color effects are achieved when high-index waveguide layer 320 features a grating depth of 175 instead of 120 nm.

Figure 14B:
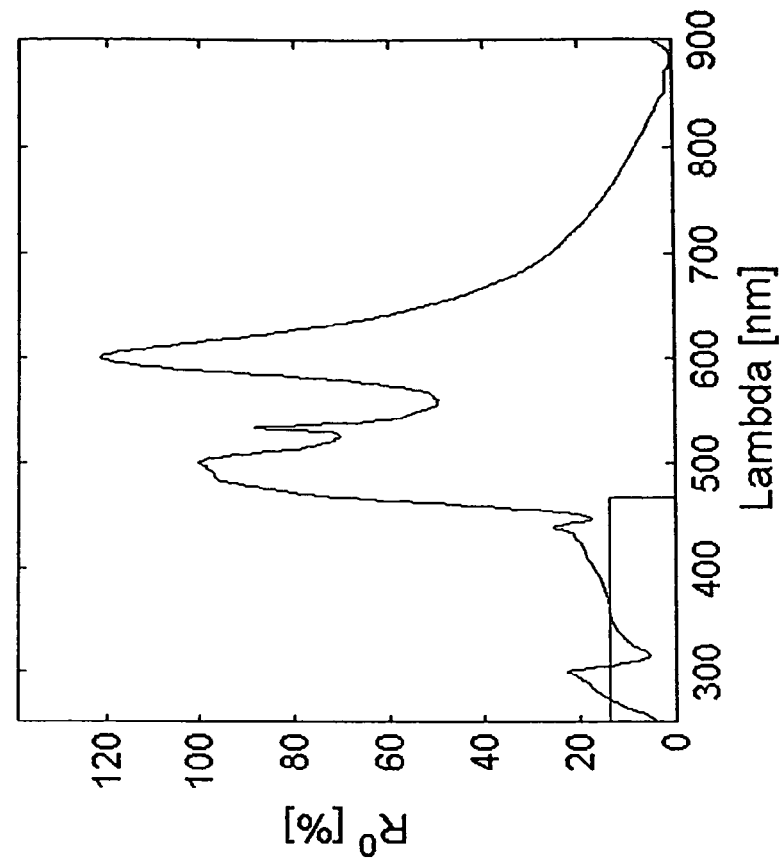
FIG. 14A and FIG. 14B each is a schematic illustration of a spectra of a light reflected from an alternative environmental sensor, respective to without adding luminescent light and with the adding luminescent light to light reflected from the sensor, according to an embodiment of this invention.
Figure 14A:
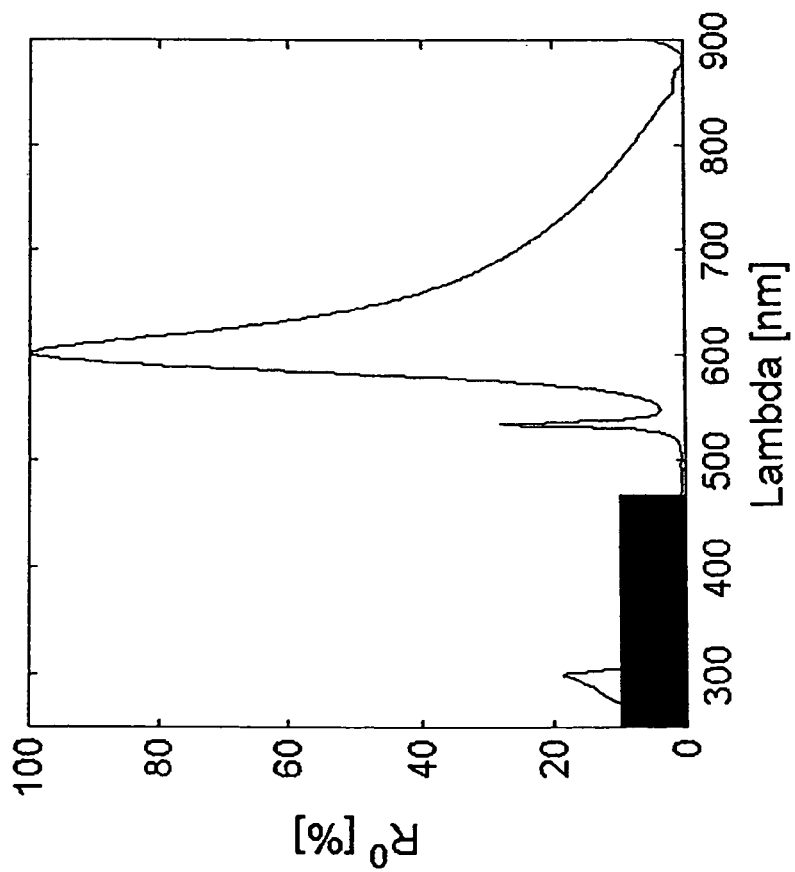

FIG. 14A and FIG. 14B each schematically illustrates an example in color change for a sensor according to an embodiment of this invention like, e.g., sensor 600, wherein in FIG. 14A, no dye emission is added to light reflected from ZOF 600, and whereas in FIG. 14B dye emission is superpositioned to light reflected from ZOF 600, i.e., reactive material 650 may be embodied or comprise the dye. As shown, a change in the reflected spectra from red to nearly white can be observed, for the following parameters of high-index waveguide layer 620: period=450 nm, grating depth=175 nm, grating shape rectangular, index of refraction of high-index waveguide layer 620 $n_{high}$=2.3 and thickness of high-index waveguide layer 620 c=100 nm. The incidence angle of light=15° and the luminescent dye Perylene.

Figure 15B:
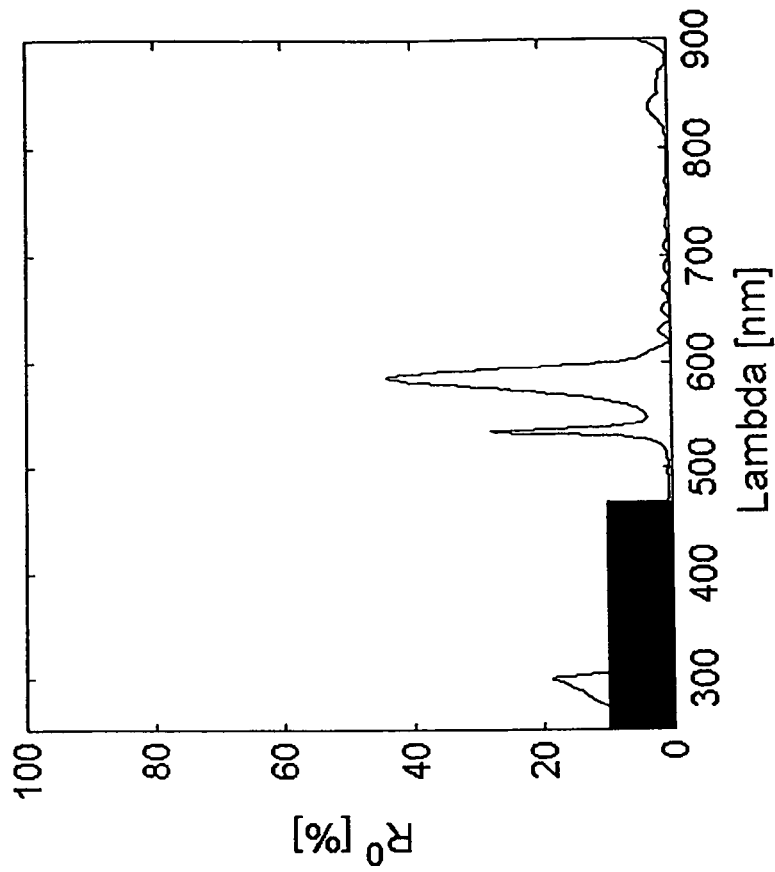
FIG. 15A and FIG. 15B each is a schematic illustration of a spectra of light reflected from a yet alternative environmental sensor, respective to without adding luminescent light and with adding luminescent light to light reflected from the sensor, according to an embodiment of this invention.
Figure 15A:
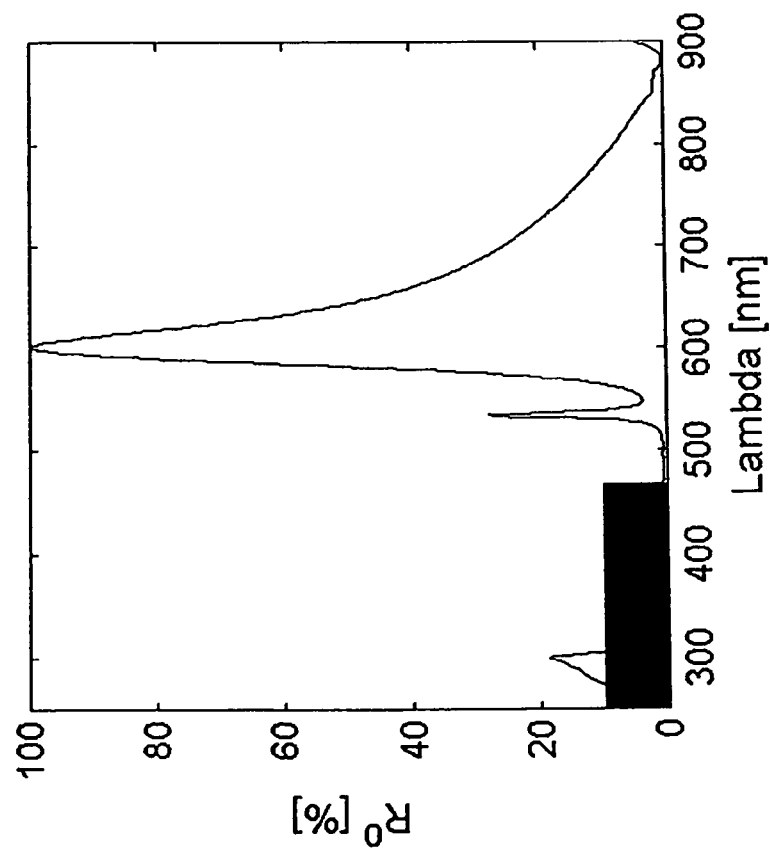

Referring to FIG. 15A and FIG. 15B, a sensor according to embodiments of this invention such as, for example, sensor 300 may include reactive material 350, which be embodied by an absorption-changing material, the absorption parameters of which may be modified upon reaction with different environments. For example, the absorption coefficient of the absorption-changing material, which may also at least partially comprise a luminescent dye (e.g., Perylene) optionally effecting additional red-absorbing properties, may change from transparent to red-absorbing. Parameters of sensor 300 employed respective of FIG. 15A and FIG. 15B are in this particular embodiment: Period=450 nm, grating depth=175 nm, grating shape rectangular, incidence angle=15°, index of refraction of high-index waveguide layer 320 $n_{high}$=2.3, and thickness of high-index waveguide layer 320 c=100 nm. Clearly, the difference in absorption prior the exposure of reactive material 350 (FIG. 15A), and after exposure (FIG. 15B) to media may effect a red to brown change in the spectrum of light reflected from sensor 300.

Figure 16:
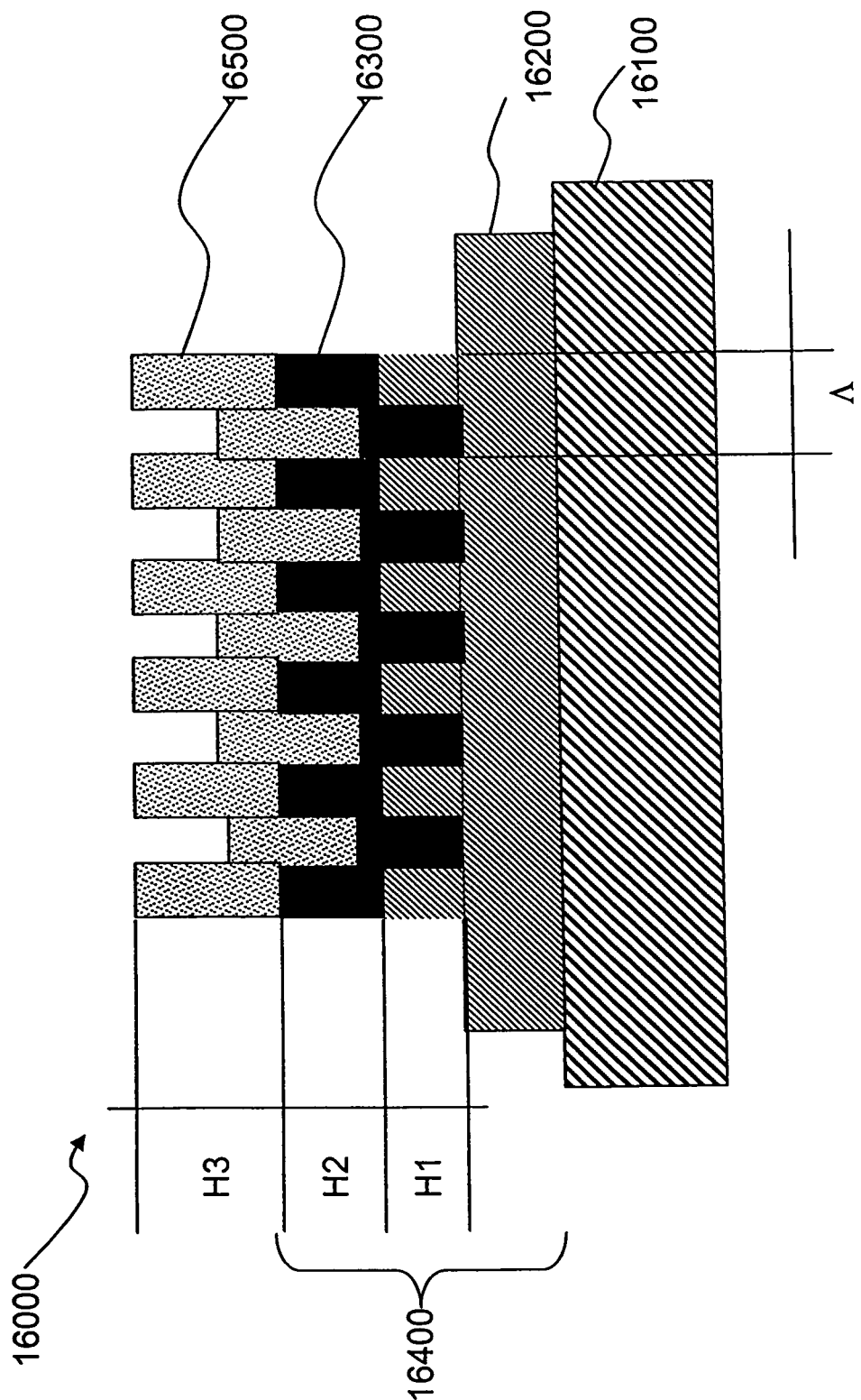
FIG. 16 is a schematic illustration of a further alternative optical environmental sensor, according to an embodiment of this invention.

FIG. 16 shows a method for manufacturing a sensor according to an embodiment of this invention, for example, a sensor 16000 comprising ZOF structure 16400 as outlined below. It should be noted that merely to simplify the discussion that follows, the methods are outlined with reference to sensor 16000 but they may also be applicable for the manufacturing of sensors according to other embodiments of this invention like, for example, sensor 300. Sensor 16000 includes a substrate 16100, on top of which a low-index material 16200 is provided. Further, a high-index waveguide layer 16300 is provided on low-index material 16200. Finally, a reactive material 16500 is provided on high-index waveguide layer 16300. Low-index material 16200 and high-index waveguide layer 16300 constitute or form a ZOF structure 16400.

The following method for manufacturing sensor 16000 processes may be employed: replication, hot-embossing or cold-embossing, thin layer evaporation, sputtering, spin coating, printing, dip-coating or die-coating and the like. Fabrication of subwavelength diffractive gratings to obtain structured ZOF 16400 may include replication techniques like, e.g., embossing, UV casting, molding, or dry etching. Highindex and low-index materials may be deposited by a thin film deposition process like, for example, sputtering, evaporation, spin coating, printing or dip-coating or die-coating.

According to embodiments of this invention, low-index material 16200 provided on substrate 16100 (made of e.g., glass) may be manufactured by sol-gel replication from a grating shim and followed by a ZnS evaporation of high-index waveguide layer 16300.

If some spacer-layers made (not shown) of thin films between ZOF structure 16400 and reactive material 16500 are used to enhance the color change effects, these spacer-layers can be made by conventional evaporation or sputtering, or spin coating, printing or dip-coating or die-coating process. Height H1 may be, for example, 130 nm; H2 may be for example, 150 nm and H3 may be, for example, 200 nm. The period Λ may be for example 270 nm.

Reactive material 16500 may be deposited by printing, adsorption, spin coating, dipping or soaking processes. Vacuum deposition processes, like Plasma Enhanced Chemical Vapor Deposition (PECVD) may also be employed. If reactive material 16500 is embodied by some porous material, e.g., to increase optical responsiveness to environmental changes, like porous Sol-gel or Silicon, or any porous aerogel, reactive material 16500 may be deposited using for example spin-coating or dip- or die-coating process. Additionally or alternatively, reactive material 16500 may be subjected to some specific treatment to render reactive material 16500 more optically sensitive to environmental changes. Some of the fabrication techniques are capable for roll-to-roll mass production. For example, the grating structure replication step can be hot-embossed or UV-embossed in PC-foil or in an embossable lacquer coated on a PET-foil and a high index layer of for example, $TiO_2$ or ZnS can be evaporated.

Reactive material 16500 may then be deposited by employing e.g. by gravure printing or spray coating on ZOF structure 16400.

According to embodiments of this invention, reactive material 16500 may be embodied by a chemically sensitive dye layer such as, for example, Bromocresol Purple (BCP), which is a pH indicator, and which may be used as the chemical dye to detect for example ammonia gas. Providing BCP may be accomplished for example as follows: a solution of BCP (0.5% (w/v)) and PMMA (5% (w/v)) in Butyl Acetate is spin coated on top of ZOF structure 16400 at, e.g., 3000 rpm. The thickness of this BCP layer is approximately 200 nm. In embodiments of this invention, half of sensor 16000 was encapsulated (not shown) so that the BCP film is in contact with neutral atmosphere (not shown). Encapsulation may be accomplished by first applying a ring (not shown) of UV curable sol-gel material and by then adhesively coupling a second glass substrate (not shown) on the ring to sensor 16000. Because the encapsulated may not be subjected to changes in environment in contrast to non-encapsulated area, reference color effects between for example neutral atmosphere and ammonia atmosphere for example become visible.

Figure 17:
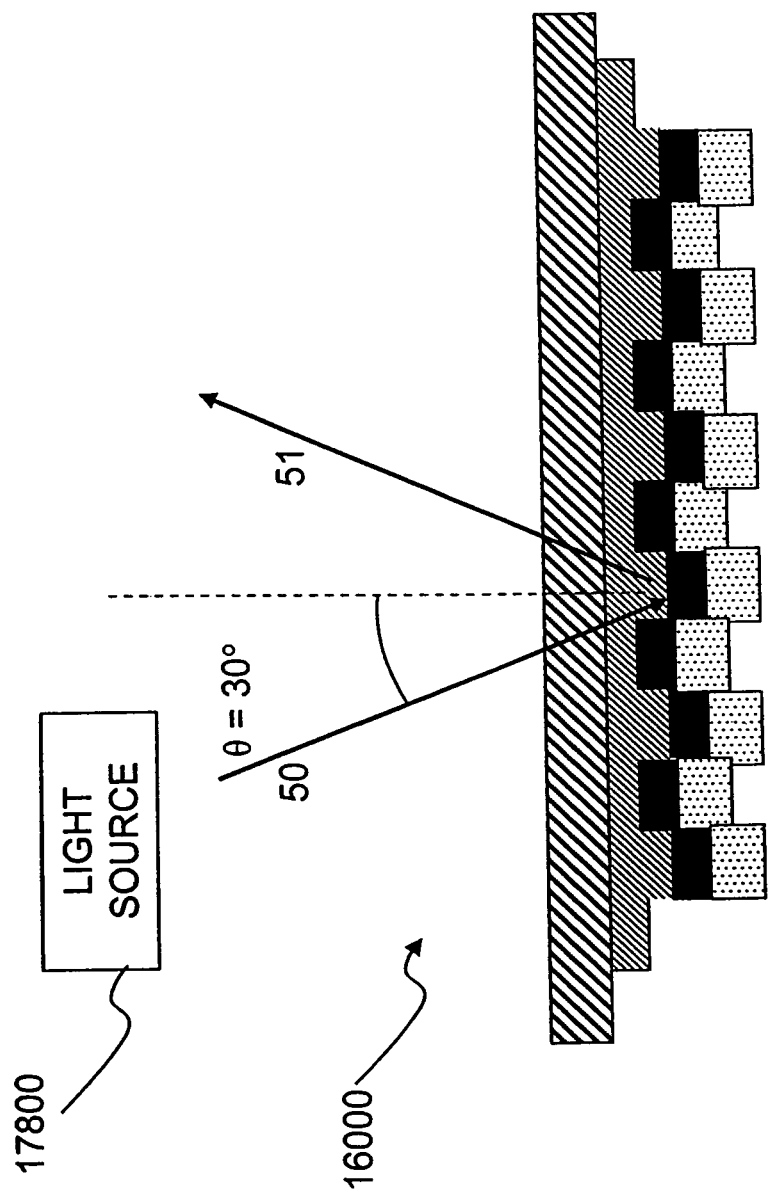
FIG. 17 is a schematic illustration of employing the optical environmental sensor of FIG. 16 for detecting changes in the environment.
Figure 18:
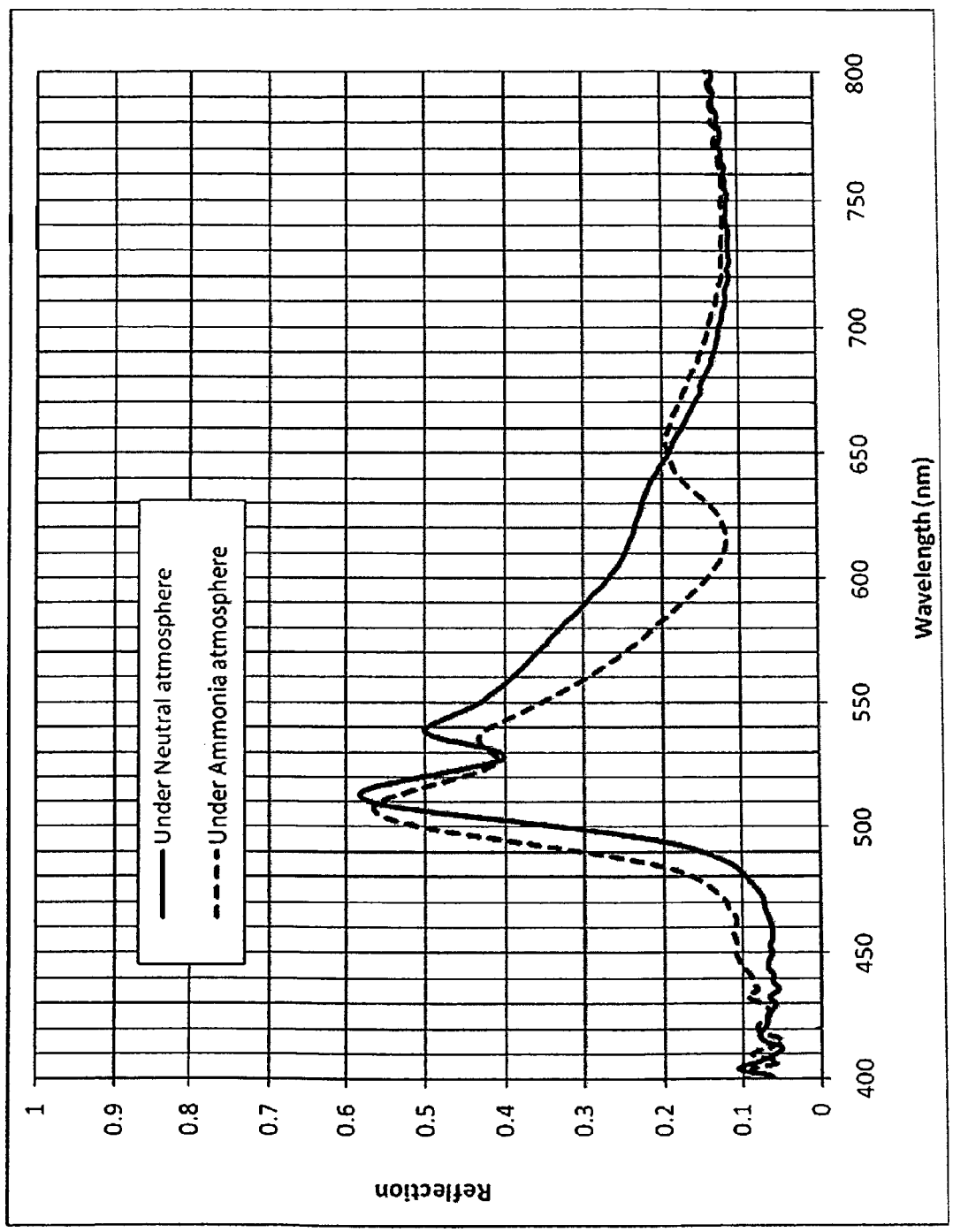
FIG. 18 is a schematic illustration of light reflected from the optical environmental sensor for different environments, according to an embodiment of this invention.

Referring to FIG. 17 and FIG. 18, spectrum measurements of light 50 reflected from the backside of sensor 16000 of the upon neutral and ammonia atmosphere have been performed. A light source 17800 may include a Halogen lamp from e.g., Mikropack connected to an optical fiber (not shown) from e.g., Ocean optics (400 um core diameter). Light coming out of the fiber was collimated with a microscope objective to obtain incident light 50 incident on the backside of sensor 16000 at an incident angle of θ=30°. Incident light 50 may be polarized, e.g., with a Glan Thomson polarizer (not shown) to select the TE mode (light parallel to the grating lines). A lens (not shown) collects and focuses reflected light 51 onto another optical fibre (not shown) connected to a spectrometer (not shown) (e.g., PCS-VIS-version 11B from SpectroSolution). The integration time of the spectrometer may be set to 20 ms.

As schematically illustrated in FIG. 18, reflected light 51 has different spectra respective of the neutral and ammonia atmosphere, which are caused due to the shift in absorption of the BCP in the different atmospheres. The obtained color shift of the reflected light can clearly be seen with the naked eye (from light green-yellow to bright green).

While this invention has been described with respect to a limited number of embodiments, these should not be construed as limitations on the scope of this invention, but rather as exemplifications of some of the embodiments. Those skilled in the art will envision other possible variations, modifications, and programs that are also within the scope of this invention. Accordingly, the scope of this invention should not be limited by what has thus far been described.

U.S. Provisional Patent Application No. 61/043,636 filed on 9 Apr. 2008, the priority document corresponding to this invention, to which a foreign priority benefit is claimed under Title 35, United States Code, and its entire teachings are incorporated, by reference, into this specification.

What is claimed is:

1. A sensor responsive to changes to a surrounding environment, the sensor comprising:
    a zero-order diffractive grating that provides reflected and/or transmitted light;
    a reactive material coupled to the zero-order diffractive grating; and
    a protective cover covering a first portion of the reactive material to insulate the first portion of the reactive material from changes in the surrounding environment and leave a second, complementary non-covered portion of the reactive material exposed to the changes;
    wherein a change in a characteristic of the reflected and/or transmitted light from the second portion relative to reflected and/or transmitted light respectively from the first portion indicates a change in the surrounding environment.

2. The sensor of claim 1, wherein said reactive material is embedded in the zero-order diffractive color filter.

3. The sensor according to claim 1, wherein the second portion of the reactive layer interacts with at least one of the following components of the environment selected from a group consisting of: gaseous components, liquid components, solid components, and any combination thereof.

4. The sensor according to claim 1, wherein the reactive material has a porous structure.

5. The sensor according to claim 4, wherein the reactive material comprises a swelling material.

6. The sensor according to claim 1, wherein the sensor is in a form of pigments.

7. The sensor according to claim 6, wherein the sensor is used in printing inks.

8. The sensor according to claim 1, further comprising interaction-promoting molecules enabling a selective binding of corresponding molecules.

9. The sensor according to claim 1, wherein the reactive material changes a characteristic of the transmitted and/or reflected light in response to an environmental change selected from a group consisting of: a change in pH, humidity, temperature, pressure, chemical composition, incident electromagnetic radiation, electrical characteristics, and any combination thereof.

10. The sensor according to claim 1, wherein the protective cover is selected from at least one member of a group consisting of: a glass substrate, polymer foil substrate, and any combination thereof.

11. The sensor according to claim 1, wherein the characteristic of the reflected and/or transmitted light is intensity.

12. The sensor according to claim 1, wherein the characteristic of the reflected and/or transmitted light is color.

13. The sensor according to claim 1, wherein the Zero-order diffractive color filter comprises a high-index waveguide layer having a diffractive grating structure surrounded by a low-index material.

14. The sensor of claim 13, wherein said reactive material is spaced away from the interface of said high-index waveguide layer with said low-index material.

15. The sensor of claim 13, wherein said reactive material constitutes the high-index waveguide layer.

16. The sensor according to claim 13, comprising a spacer layer that is positioned between the high-index waveguide layer and the reactive material.

17. A sensor indicating a change in an environment surrounding the sensor, the sensor comprising:
    a Zero-order diffractive color filter providing a first visible color prior to the change in the environment and a second visible color that is different from the first visible color after the change in the environment, the Zero-order diffractive color filter comprising:
    an index of refraction waveguide layer including a Zero-order diffractive grating structure;
    a reactive material layer in contact with the environment and that reacts to a change in the environment; and
    a protective cover covering a part of the reactive material to obtain a sensing area and a non-sensing area of the sensor;

the reactive material to change the Zero-order diffractive filter of the sensing area from the first visible color to the second visible color, wherein the non-sensing area does not exhibit substantial color change with change in the environment.

18. The sensor according to claim 17, wherein the protective cover is selected from at least one member of a group consisting of: a glass substrate, polymer foil substrate, and any combination thereof.

19. A sensor indicating a change in an environment surrounding the sensor, the sensor comprising:
- a first outer surface and a second outer surface opposite the first outer surface;
- an index of refraction waveguide layer including a Zero-order diffractive grating structure, the waveguide layer disposed between the first outer surface and the second outer surface;
- a reactive material that reacts to change in the environment;
- the reactive material providing change in a visible optical property of at least one surface selected from a group consisting of: the first outer surface, and the second outer surface in response to a change in the environment;
- a protective cover covering a part of the at least one surface to obtain a non-sensing area adjacent to a complementary sensing area, the non-sensing area remaining substantially non-responsive and the sensing area being responsive to a change in the environment.

* * * * *